United States Patent
Park

(10) Patent No.: US 9,943,324 B2
(45) Date of Patent: Apr. 17, 2018

(54) SURGICAL INSTRUMENT, AND MEDICAL KIT FOR TREATING CARPAL TUNNEL SYNDROME

(76) Inventor: Jong Ha Park, Busan (KR)

( * ) Notice: Subject to any disclaimer, the term of this patent is extended or adjusted under 35 U.S.C. 154(b) by 1043 days.

(21) Appl. No.: 14/406,269

(22) PCT Filed: Oct. 10, 2011

(86) PCT No.: PCT/KR2011/007477
§ 371 (c)(1),
(2), (4) Date: Dec. 8, 2014

(87) PCT Pub. No.: WO2013/054953
PCT Pub. Date: Apr. 18, 2013

(65) Prior Publication Data
US 2015/0133982 A1 May 14, 2015

(30) Foreign Application Priority Data
Oct. 10, 2011 (KR) .................. 10-2011-0102818

(51) Int. Cl.
*A61B 17/32* (2006.01)
(52) U.S. Cl.
CPC .................... *A61B 17/320036* (2013.01)
(58) Field of Classification Search
None
See application file for complete search history.

(56) References Cited

U.S. PATENT DOCUMENTS

| | | | |
|---|---|---|---|
| 5,522,827 A * | 6/1996 | Combs | A61B 17/00008 606/167 |
| 5,730,749 A * | 3/1998 | Battenfield | A61B 17/320036 606/167 |
| 5,769,865 A * | 6/1998 | Kermode | A61B 17/320036 128/898 |
| 6,530,933 B1 | 3/2003 | Yeung et al. | |
| 6,626,916 B1 | 9/2003 | Yeung et al. | |
| 8,753,364 B2 * | 6/2014 | McCormack | A61B 17/320036 600/439 |
| 9,314,260 B2 * | 4/2016 | Porshinsky | A61B 17/320036 |
| 9,381,033 B2 * | 7/2016 | Guo | A61B 17/320036 |
| 2001/0049527 A1 | 12/2001 | Cragg | |

(Continued)

FOREIGN PATENT DOCUMENTS

JP 2001-70315 A 3/2001
JP 2010-512191 A 4/2010
(Continued)

OTHER PUBLICATIONS

International Searching Authority, International Search Report for PCT/KR2011/007477 dated Oct. 24, 2012 [PCT/ISA/210].
(Continued)

*Primary Examiner* — Amy R Weisberg
(74) *Attorney, Agent, or Firm* — Sughrue Mion, PLLC

(57) ABSTRACT

A surgical instrument providing a passage to upper and lower portions of the flexor retinaculum, comprises: a hollow cannular needle having an end capable of penetrating the skin; and a blunt rod which enters the cannular needle and moves under the skin in correspondence to the passage, wherein the cannular needle can move along the blunt rod moved under the skin so as to provide the passage to upper and lower portions of the flexor retinaculum.

3 Claims, 7 Drawing Sheets

(56) References Cited

U.S. PATENT DOCUMENTS

| | | | |
|---|---|---|---|
| 2006/0089609 A1 | 4/2006 | Bleich et al. | |
| 2008/0033465 A1* | 2/2008 | Schmitz | A61B 17/1604 |
| | | | 606/170 |
| 2008/0045989 A1 | 2/2008 | Welborn | |
| 2008/0051812 A1* | 2/2008 | Schmitz | A61B 17/1671 |
| | | | 606/167 |
| 2009/0048620 A1* | 2/2009 | Weiss | A61B 17/320036 |
| | | | 606/167 |
| 2011/0087255 A1* | 4/2011 | McCormack | A61B 5/04005 |
| | | | 606/167 |
| 2013/0131454 A1* | 5/2013 | McCormack | A61B 1/00188 |
| | | | 600/162 |
| 2013/0165962 A1* | 6/2013 | Porshinsky | A61B 17/320036 |
| | | | 606/185 |
| 2013/0289597 A1* | 10/2013 | Guo | A61B 17/320036 |
| | | | 606/170 |

FOREIGN PATENT DOCUMENTS

| | | |
|---|---|---|
| KR | 10-2006-0132588 A | 12/2006 |
| WO | 2011/017665 A2 | 2/2011 |

OTHER PUBLICATIONS

International Searching Authority, Written Opinion for PCT/KR2011/007477 dated Oct. 24, 2012 [PCT/ISA/237].

\* cited by examiner

[Fig. 1]
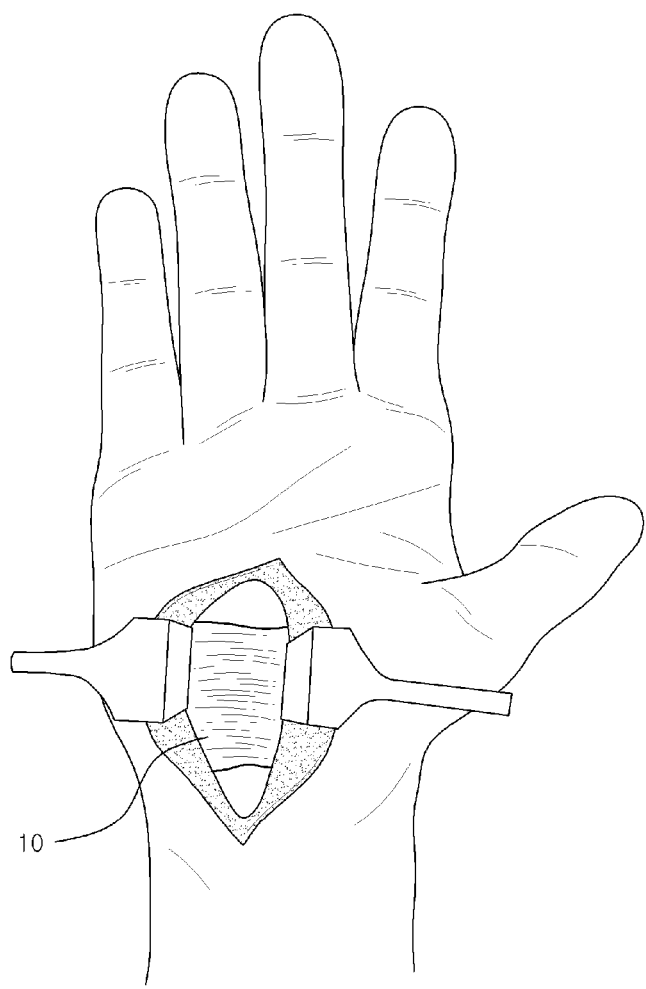

[Fig. 2]
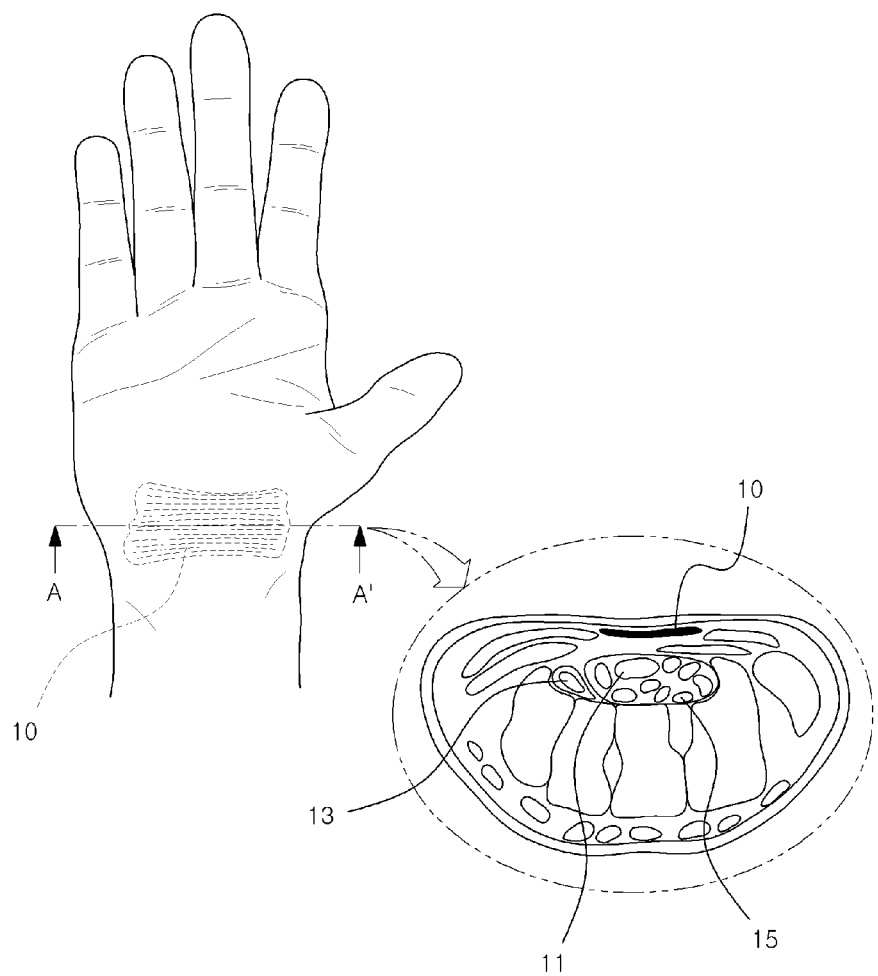

[Fig. 3]
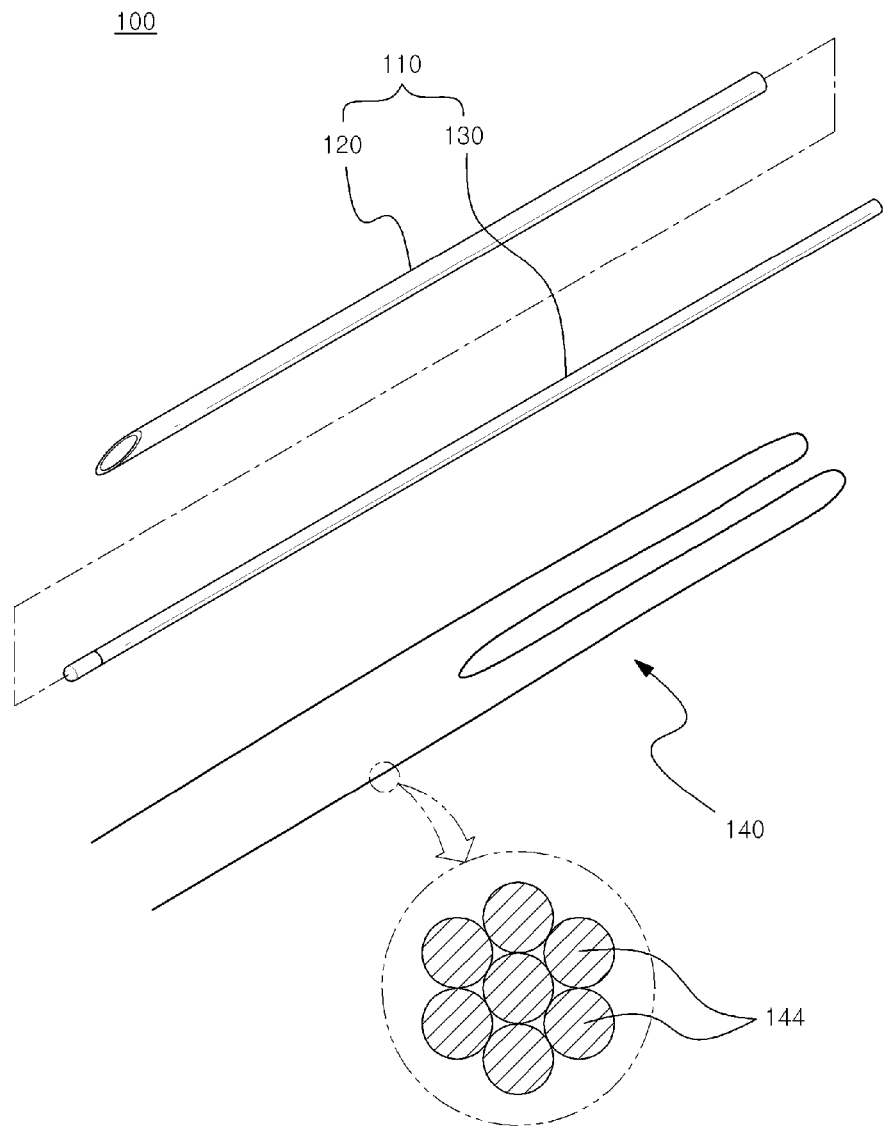
[Fig. 4]
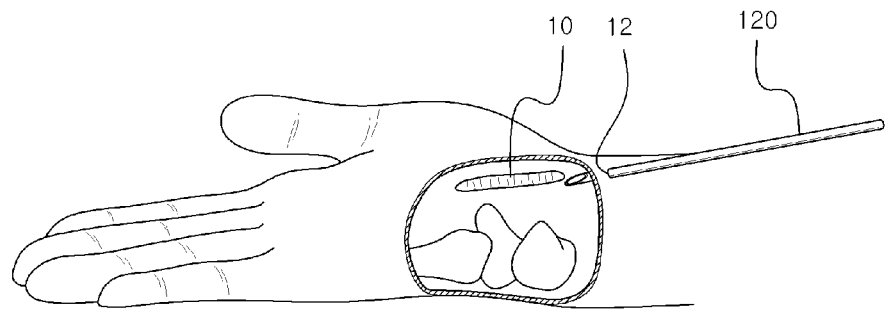

[Fig. 5]
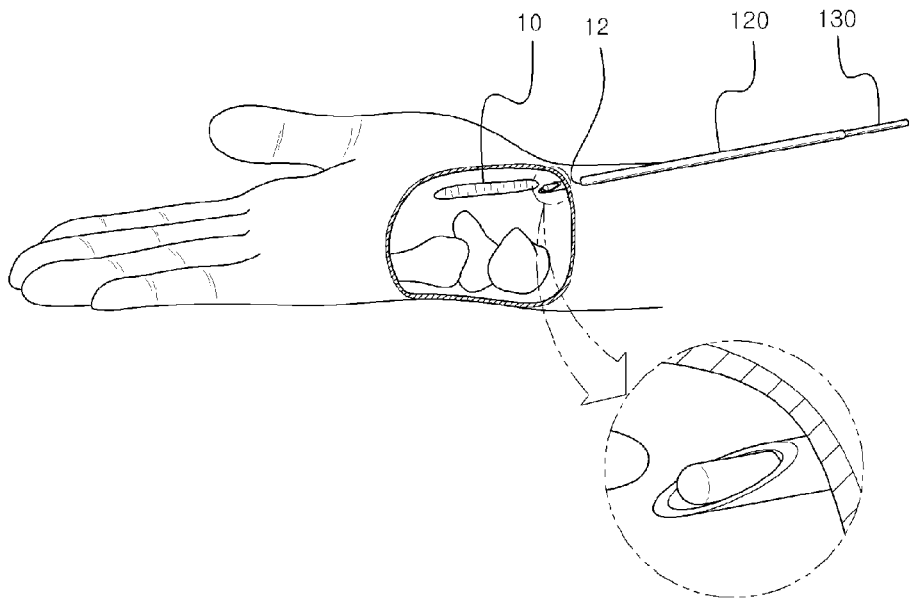
[Fig. 6]
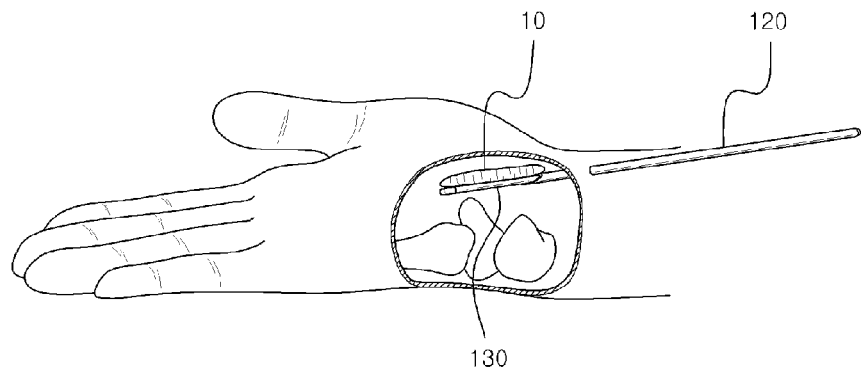
[Fig. 7]
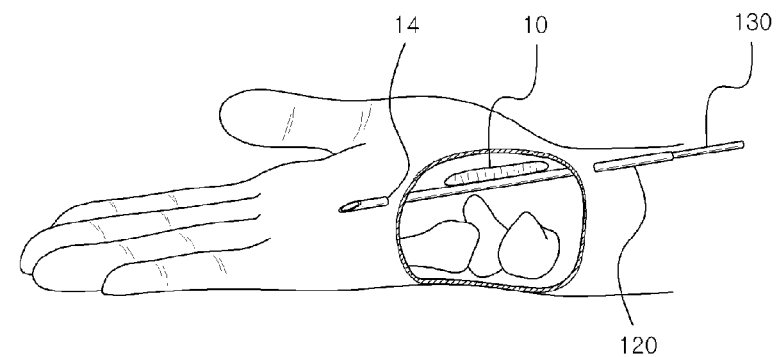

[Fig. 8]
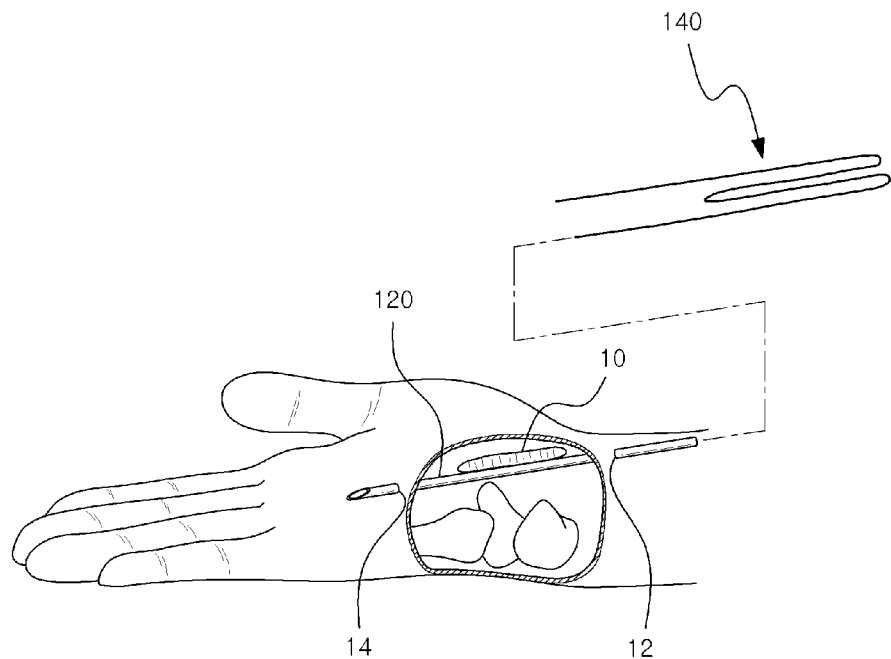
[Fig. 9]
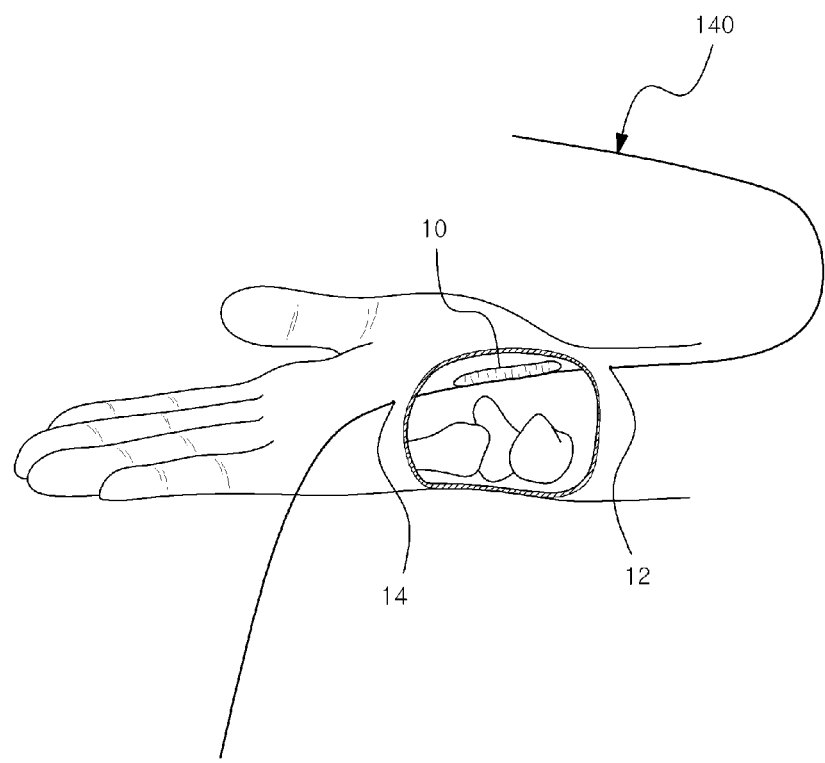

[Fig. 10]
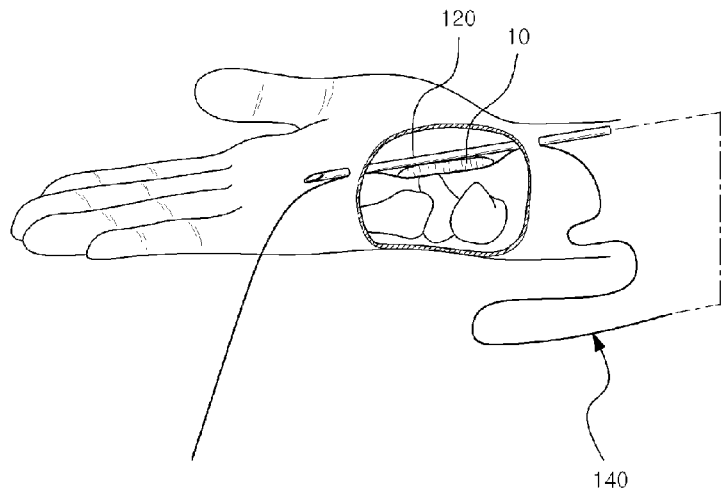
[Fig. 11]
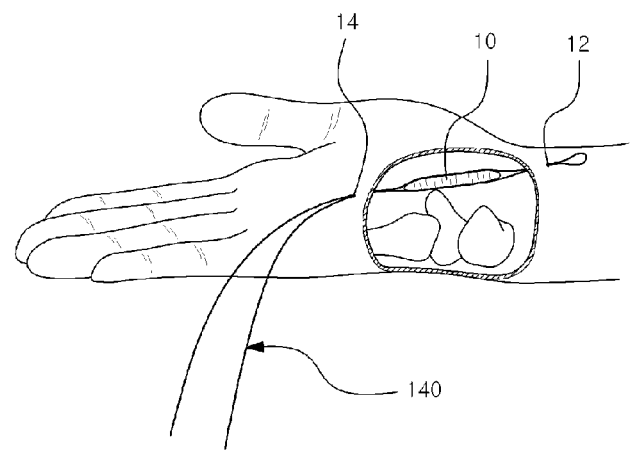
[Fig. 12]
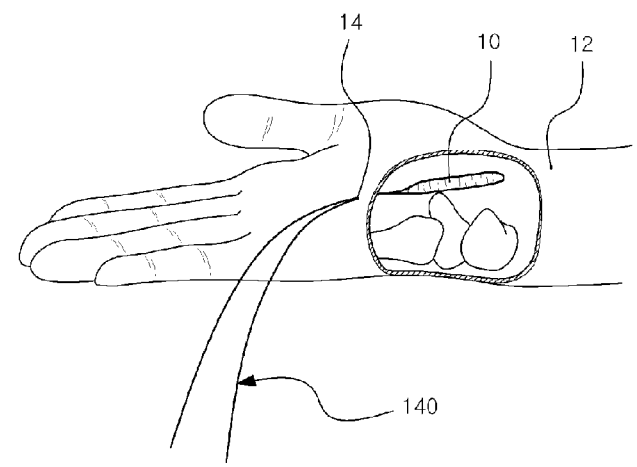

[Fig. 13]
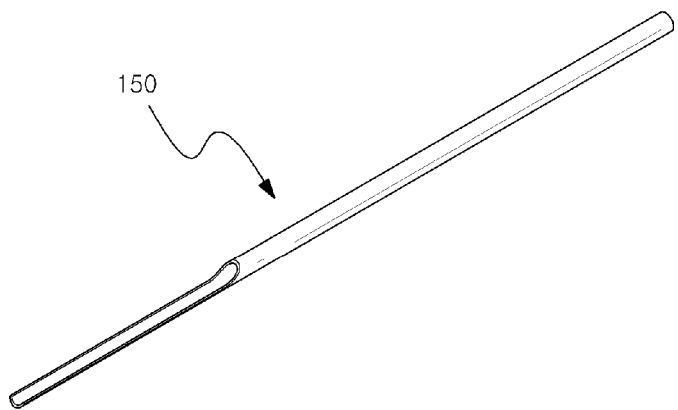
[Fig. 14]
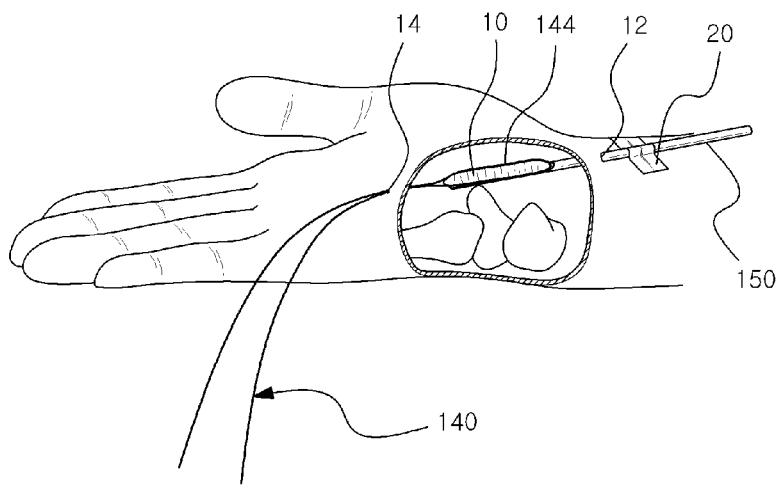

SURGICAL INSTRUMENT, AND MEDICAL KIT FOR TREATING CARPAL TUNNEL SYNDROME

CROSS-REFERENCE TO RELATED APPLICATIONS

This application is a 371 of PCT Patent Application PCT/KR2011/007477 filed Oct. 10, 2011 which claims priority to Republic of Korea application 10-2011-0102818 filed Oct. 10, 2011.

TECHNICAL FIELD

The present disclosure relates to a surgical instrument that can be used in conducting an operation for cutting flexor retinaculum that passes over the carpal tunnel and, also relates to a medical kit for treating carpal tunnel syndrome.

BACKGROUND OF THE INVENTION

The carpal tunnel is a small passageway in the wrist under the skin consisting of bones and tendons of the wrist on the palmar side of the wrist. Nine tendons and one nerve pass through the carpal tunnel toward the hand. If the carpal tunnel is narrowed or the internal pressure thereof is increased for some reasons, the median nerve passing through the carpal tunnel would be compressed, resulting in various symptoms in palm and fingers in the distribution of the median nerve, i.e., a common medical condition known as carpal tunnel syndrome.

At the initial stage of the carpal tunnel syndrome, the symptoms can be fixed by injecting steroids into the carpal tunnel. If, however, the disease more develops and cannot be cured by the steroids injection, surgical treatment through should be considered.

Conventionally, it has been attempted to treat the carpal tunnel syndrome through a surgical operation of incising the skin of the wrist so as to expose flexor retinaculum 10 that arches over the carpal tunnel and cutting a part of the flexor retinaculum 10. This surgery, however, has problems in that the incision range of the skin is excessively wide and recovery takes long time.

In this regard, recently, an endoscopic operation of inserting an endoscope to a space below the flexor retinaculum and cutting the flexor retinaculum is attempted. This surgery, however, is also problematic in that the incision site for the insertion of the endoscope is still not small enough, the operation time is long due to many difficulties in cutting the flexor retinaculum, and recovery still takes a quite long time.

DISCLOSURE

Technical Problem

The present disclosure is provided to solve the problems mentioned above. An object of the present disclosure is to provide a surgical instrument for use in treating carpal tunnel syndrome and capable of cutting flexor retinaculum while minimizing skin incision and, also, to provide a medical kit for treating carpal tunnel syndrome.

Technical Solution

In accordance with an exemplary embodiment of the present disclosure, there is provided a surgical instrument that provides a passageway to above and below flexor retinaculum, comprising a hollow cannular needle having a leading end capable of penetrating into skin; and a blunt rod configured to be inserted into the cannular needle and moved under the skin in correspondence to the passageway, wherein the cannular needle can move along the blunt rod moved under the skin to provide the passageway.

In general, a method of cutting hypertrophied flexor retinaculum is selected as a surgical way to treat carpal tunnel syndrome. For example, flexor retinaculum may be directly cut with a scalper after incising the skin of the wrist that covers the flexor retinaculum, or an endoscope may be put into a space below the flexor retinaculum and cut the flexor retinaculum partially from below. In these methods, however, the skin incision range is wide and thus, recovery takes long.

However, by using the above-described surgical instrument of the exemplary embodiment, the passageway leading to positions right above and below the flexor retinaculum is formed, and the wire-shaped cutting member is inserted into the passageway. Then, by using the cutting member arranged to surround the flexor retinaculum in a direction perpendicular to the lengthwise direction of the flexor retinaculum, the flexor retinaculum can be easily cut. When the flexor retinaculum is cut by using the wire-shaped cutting member, the skin is punctured only with a size corresponding to the diameter of the cannular needle. Thus, the recovery time can be greatly reduced.

The cannular needle may have a sharp leading end so as to easily penetrate into the skin and be inserted inner to the skin. Further, the cannular needle may have a sufficiently long length such that an end thereof can be exposed out of the skin at front (or rear) side of the flexor retinaculum after penetrated into the skin from the rear (or the front) side of the flexor retinaculum.

Meanwhile, a position into which the cannular needle can be inserted may be previously checked before inserting the cannular needle by penetrating into the skin from the front and the rear of the flexor retinaculum. This can be accomplished by using ultrasonography. To be specific, since the flexor retinaculum is located at the wrist crease, the position through which the cannular needle penetrates into the skin may be formed at a position near the wrist crease. To be more specific, the position may be closely near the palmaris longus just ulnar side or little finger side. The position checked in this way may be marked on the skin of the palm.

The blunt rod may have an appropriate diameter such that it can be inserted into the cannular needle. After inserted into the cannular needle, the blunt rod may be moved from the front to the rear of the flexor retinaculum passing through above and below the flexor retinaculum.

The blunt rod is moved in correspondence to the passageway led to above and below the flexor retinaculum, and the cannular needle is then moved along the blunt rod such that the leading end of the cannular needle is arranged at the rear of the flexor retinaculum.

Thereafter, if the cannular needle exits out of the skin, the passageway can be formed above and below the flexor retinaculum.

Here, the blunt rod provides the path through which the cannular needle can be guided in advance to minimize unnecessary damage on the ulnar artery, the median nerve or other body tissues adjacent to the wrist. Since the blunt rod has a blunt end, the damage can be minimized when moving the blunt rod from the front to the rear of the flexor retinaculum.

Further, in accordance with another exemplary embodiment, there is provided a medical kit for treating carpal tunnel syndrome, which provides a passageway to above and below flexor retinaculum and is configured to cut the flexor retinaculum, comprising a hollow cannular needle having a leading end capable of penetrating into skin; a blunt rod configured to be inserted into the cannular needle and moved under the skin in correspondence to the passageway; and a wire-shaped cutting member configured to be inserted into the passageway and arranged to surround the flexor retinaculum, the passageway being formed at above and below the flexor retinaculum by the cannular needle moved along the blunt rod, wherein the flexor retinaculum is cut by the cutting member in a state that the cutting member is arranged to surround the flexor retinaculum and the cannular needle is removed.

The cutting member may be implemented by a single wire or a plurality of wires braided together. If the cutting member is made up of the plurality of wires that are braided into a single wire-shaped member, the cutting member is less likely to be cut off during the process of cutting the flexor retinaculum. Further, the cutting member may have prominences on the surface thereof to thereby have roughness suitable for cutting the flexor retinaculum. The number of the wires included of the cutting member may be, desirably, six to seven. However, the number of the wires may be modified in various ways depending on the required degree of strength or roughness. These wires may be made of any of various materials such as stainless steel, steel wires, copper wires and synthetic resins as long as those materials do not have toxicity and can be inserted into the human body.

The cutting member can be inserted into the passageway formed at above and below the flexor retinaculum by means of the above-described surgical instrument. By repeatedly moving the cutting member, which is arranged over the superficial portion and the lower portion of the flexor retinaculum, back and forth, and thereby sawing the flexor retinaculum with the cutting member, the flexor retinaculum can be cut.

Here, the way to place the cutting member to surround the flexor retinaculum over the superficial portion and the lower portion thereof will be discussed. In the following description, the terms "front" and "rear" are relative concepts and can be used reversely. Below, however, the position at the flexor retinaculum close to the elbow (in other words, the proximal part) will be defined as the front, while the position at the flexor retinaculum close to finger tips (in other words, the distal part) will be referred to as the rear.

To be specific, the cannular needle is inserted through the skin at the front of the flexor retinaculum such that the leading end of the cannular needle is located adjacent to the lower portion of the flexor retinaculum. Then, the blunt rod is inserted into the cannular needle and moved from the proximal part to the distal part, and the cannular needle is moved along the blunt rod below the flexor retinaculum from the front to the rear of the flexor retinaculum. With the cannular needle exposed out of the skin, the blunt rod is removed. Then, one end of the cutting member is inserted into the cannular needle through an end at the front of the flexor retinaculum and taken out of the cannular needle through the other end at the rear of the flexor retinaculum. Then, if the cannular needle is removed, the cutting member is arranged below the flexor retinaculum perpendicularly to the lengthwise direction of the flexor retinaculum. Here, the direction in which the cannular needle passes below the flexor retinaculum may be from the front to the rear or vice versa. Further, the insertion direction of the cutting member inserted into the cannular needle may also be reversed to that described above.

In this state, the cannular needle is inserted through the skin again at the front of the flexor retinaculum such that its leading end is located adjacent to the superficial portion of the flexor retinaculum. Thereafter, the blunt rod is inserted into the cannular needle and pushed from the proximal part toward the distal part. The cannular needle is moved along the blunt rod above the flexor retinaculum from the front to the rear of the flexor retinaculum. Then, with the cannular needle exposed out of the skin, the other end of the same cutting member is inserted into the cannular needle and taken out of the cannular needle from the front to the rear of the flexor retinaculum. Then, if the cannular needle is removed, the cutting member is arranged above the flexor retinaculum in a direction perpendicular to the lengthwise direction of the flexor retinaculum. As a result, both ends of the cutting member are exposed at the rear of the flexor retinaculum. Here, the direction in which the cannular needle penetrate through above the flexor retinaculum may be from the front to the rear or vice versa, and the insertion direction of the cutting member inserted into the cannular needle may also be reversed as that described above. Furthermore, in the above description, the cannular needle is made to pass through the space below the flexor retinaculum first and, then, made to pass through the space above the flexor retinaculum. However, this order may also be reversed. The insertion direction of the cannular needle and the insertion direction of the cutting member may be modified in various ways as long as the cutting member can be arranged to surround the flexor retinaculum in a U-shaped over the upper and lower portions thereof.

Through the above-described processes, the cutting member can be arranged to surround the flexor retinaculum as in a U-shape. Then, by holding both ends of the cutting member and sawing the flexor retinaculum with the cutting member, it is possible to cut the flexor retinaculum.

For reference, in the prior art, two puncture holes might be formed on the skin by the cannular needle at each of the front of the flexor retinaculum and at the rear of the flexor retinaculum. In the present exemplary embodiment, however, the entrance hole into which the cannular needle inserted first and the entrance hole into which the cannular needle inserted later are made to be coincident with each other so as to form only one puncture hole on the skin at the front of the flexor retinaculum. Accordingly, in the process of cutting the flexor retinaculum by repeating pulling and pushing the one end of the cutting member at the rear of the flexor retinaculum, unnecessary skin incision can be avoided.

Meanwhile, one or two puncture holes may be formed on the skin at the rear of the flexor retinaculum. At the rear of the flexor retinaculum where both ends of the cutting member are located, the cutting member may not cause unnecessary skin incision in the process of holding both ends of the cutting member and cutting the flexor retinaculum regardless of the number of the puncture holes.

Advantageous Effects

By using the surgical instrument of the exemplary embodiment, it is possible to provide a passageway to above and below the flexor retinaculum. By inserting the cutting member into the passageway and cutting the flexor retinaculum with the cutting member, unnecessary incision of the skin can be avoided except for the puncture hole through which the cutting member is inserted. Thus, skin closure after the incision is not required, and wound dressing can be done quite simply. Further, recover takes short time.

Furthermore, before inserting the cannular needle of the surgical instrument in accordance with the exemplary embodiments of the present disclosure, the position through which the cannular needle is to be inserted can be checked by using ultrasonography. Thus, the injury in the skin can be minimized.

Moreover, in the process of cutting the flexor retinaculum by using the surgical instrument and the medical kit in accordance with the exemplary embodiments of the present disclosure, the cutting member may be arranged to surround the flexor retinaculum from below and above it. Thus, it is possible to cut the flexor retinaculum completely in the direction perpendicular to the lengthwise direction of the flexor retinaculum.

In addition, in the medical kit of the exemplary embodiments of the present disclosure, since the cutting member is provided in the form of wire, injury or damage on ambient body cells near the flexor retinaculum can be minimized when sawing the flexor retinaculum with the cutting member, unlike a conventional protruding blade.

Moreover, since the cutting member is composed of a plurality of wires braided together in the exemplary embodiments of the present disclosure, the cutting member has sufficient strength so as not to be cut off in the process of cutting the flexor retinaculum and, also, is sufficiently flexile to tightly surround the flexor retinaculum over the upper and lower portions thereof. In addition, the cutting member may have prominences on the surface thereof, and, thus, the cutting member may have enough roughness to cut the flexor retinaculum.

BRIEF DESCRIPTION OF DRAWINGS

FIG. 1 is a diagram for describing a conventional surgical operation of treating carpal tunnel syndrome by incising the skin to expose the flexor retinaculum that arches over the carpal tunnel and cutting a part of the flexor retinaculum with a scalpel;

FIG. 2 is a cross sectional view illustrating the vicinity of the wrist where the flexor retinaculum is located;

FIG. 3 is a perspective view illustrating a configuration of a surgical instrument and a medical kit for treating carpal tunnel syndrome including the surgical instrument in accordance with an exemplary embodiment of the present disclosure;

FIG. 4 to FIG. 11 are diagrams for describing the way to insert a cutting member above and below the flexor retinaculum across the flexor retinaculum by using the surgical instrument in accordance with the exemplary embodiment of the present disclosure;

Specifically, FIG. 4 is a diagram showing a cannular needle inserted into the skin at the front of the flexor retinaculum;

FIG. 5 is a diagram illustrating a state in which a blunt rod is inserted into the cannular needle;

FIG. 6 is a diagram for describing a process in which the blunt rod is moved to the rear of the flexor retinaculum through a space below the flexor retinaculum;

FIG. 7 is a diagram for describing a process in which the cannular needle penetrates the skin at the rear of the flexor retinaculum, so as to be exposed out of the skin;

FIG. 8 is a diagram for describing a process in which a cutting member is inserted into the cannular needle, which is moved below the flexor retinaculum in a range from the front to the rear of the flexor retinaculum;

FIG. 9 is a diagram illustrating a state in which the cutting member is arranged below the flexor retinaculum;

FIG. 10 is a diagram for describing a process in which the cannular needle is inserted into a space above flexor retinaculum and the cannular needle is inserted into the cannular needle;

FIG. 11 is a diagram illustrating a state in which the cutting member is arranged above and below the flexor retinaculum;

FIG. 12 is a diagram for describing a process of cutting the flexor retinaculum by using the cutting member;

FIG. 13 is a perspective view of a supporting member of the medical kit for treating carpal tunnel syndrome in accordance with another exemplary embodiment of the present disclosure; and FIG. 14 is a diagram for describing the way to use the supporting member.

BEST MODE FOR THE INVENTION

Hereinafter, exemplary embodiments of the present disclosure will be described in detail with reference to the accompanying drawings. However, it is to be noted that the present disclosure is not limited to the exemplary embodiments but can be realized in various other ways. Through the whole document, like reference numerals denote like parts, and redundant parts or parts deemed to be obvious to those skilled in the art will be omitted to enhance the clarity of the description.

FIG. 3 is a perspective view illustrating a configuration of a surgical instrument and a medical kit for treating carpal tunnel syndrome including the surgical instrument in accordance with an exemplary embodiment of the present disclosure.

Referring to FIG. 3, a surgical instrument 110 is designed to provide a passageway to above and below the flexor retinaculum. The surgical instrument 110 includes a hollow cannular needle 120 having an end capable of penetrating into the skin; and a blunt rod 130 capable of being inserted into the cannular needle 120.

Conventionally, to treat carpal tunnel syndrome, the skin of the wrist that covers the flexor retinaculum is incised and the flexor retinaculum is directly cut with a scalpel, or an endoscope is inserted to below the flexor retinaculum and the flexor retinaculum is partially cut from below. However, these conventional methods have problems in that the skin incision is wide and thus recovery takes long time. With the above-described surgical instrument 110, however, by providing the passageway to above and below the flexor retinaculum and cutting the flexor retinaculum with a cutting member to be described later, the skin incision can be minimized.

A medical kit 100 for treating carpal tunnel syndrome includes the surgical instrument 110 and additionally includes a cutting member 140.

The cutting member 140 is inserted into the passageway, which is led to directly above or below the flexor retinaculum, and positioned to surround the flexor retinaculum in a direction perpendicular to the lengthwise direction of the flexor retinaculum. Accordingly, the flexor retinaculum can be easily cut. If the flexor retinaculum is cut with a wire-shaped cutting member 140, only a puncture hole having the same size as that of the cannular needle 120 is made on the skin. Thus, recovery time after the surgery can be greatly reduced. For reference, as depicted in FIG. 3, the cutting member 140 may be composed of seven wires 144 that are braided together. However, the number of the wires 144 composing the cutting member 140 can be modified to obtain desired level of strength and flexibility, and the material for the wires 144 may be selected from various materials such as stainless steel, steel wires, copper wires and synthetic resins.

The cannular needle 120 may be formed to have a sufficiently long length such that after inserted into the skin at one side (front or rear) of the flexor retinaculum, it can exit out of the skin at the other side (rear or front) of the flexor retinaculum.

The blunt rod 130 has an appropriate diameter to be inserted into the above-described cannular needle 120. The blunt rod 130 inserted into the cannular needle 120 can be pushed to above or below the flexor retinaculum from the front to the rear of the flexor retinaculum.

In this way, the blunt rod 130 is moved in correspondence to a passageway provided to above and below the flexor retinaculum, and, then, the cannular needle 120 is moved along the blunt rod 130 such that a leading end of the cannular needle 120 is positioned at the rear of the flexor retinaculum.

Thereafter, if the cannular needle 120 is forced out of the skin, a passageway to above or below the flexor retinaculum can be provided.

For reference, the reason why the path through which the cannular needle 120 can be guided is provided in advance by using the blunt rod 130 is in order not to injure the ulnar artery, the median nerve or other body tissues adjacent to the wrist while moving the blunt rod 130 having a blunt end from the front to the rear of the flexor retinaculum.

Now, referring to FIG. 4 to FIG. 11, there will be elaborated a process of inserting the cutting member to above and below the flexor retinaculum and cutting at least a part of the flexor retinaculum with the cutting member by using the surgical instrument and the medical kit for treating the carpal tunnel syndrome in accordance with the exemplary embodiment. Particularly, a method of positioning the cutting member in a U-shape to surround the flexor retinaculum over the upper and lower portions thereof will be described. The terms "front" and "rear" used in the following description are relative concepts and can be used reversely. Below, however, the position at the flexor retinaculum close to the elbow will be defined as the front, while the position at the flexor retinaculum close to finger tips will be referred to as the rear.

First, referring to FIG. 4, the cannular needle 120 is inserted to penetrate into the skin at the front of the flexor retinaculum 10. In general, the flexor retinaculum is located in the wrist crease, though it differs from person to person. Accordingly, an insertion hole 12 through which the cannular needle 120 penetrates into the skin is formed near the palmaris longus just ulnar side. To be more specific, the insertion hole 12 may be formed in the vicinity of the wrist crease next to the ulnar in a direction from the palmaris longus toward the little finger.

The cannular needle 120 is inserted up to a position below the flexor retinaculum 10. In order to avoid unnecessary damage on body tissues, the insertion position of the cannular needle 120 needs to be set accurately.

For the purpose, before the cannular needle 120 penetrating into the skin at the front or at the rear of the flexor retinaculum 10, the position through which the cannular needle 120 penetrates into the skin may be checked previously. This pre-checking may be accomplished by ultrasonography. The insertion position is the same as mentioned above, and the position checked in this way may be marked on the palm skin.

That is, in the present exemplary embodiment, the cannular needle 120 is lightly stuck into the skin such that the leading end of the cannular needle advances just to the front of the flexor retinaculum 10, as depicted in FIG. 4. Then, as shown in FIG. 5, the blunt rod 130 is inserted into the cannular needle 120 and pushed inward to be exposed from the leading end of the cannular needle 120.

Then, as depicted in FIG. 6, the blunt rod 130 inserted into the cannular needle 120 is moved below the flexor retinaculum 10 from the front to the rear of the flexor retinaculum 10.

Here, the reason why the path through which the cannular needle 120 can be guided is provided in advance by using the blunt rod 130 is to minimize damage on the ulnar artery, the median nerve or other body tissues adjacent to the wrist that might be caused when the blunt rod 130 possibly having a blunt end with a semicircular shape, for example, is moved from the front to the rear of the flexor retinaculum 10.

Thereafter, the cannular needle 120 is moved along the blunt rod 130 which is advanced to the rear of the flexor retinaculum 10, and, then, is exposed out of the skin by penetrating out of the skin at the rear of the flexor retinaculum 10, as depicted in FIG. 7. As a result, an exposure hole 14 is formed in the skin at the rear of the flexor retinaculum 10.

Afterwards, the blunt rod 130 is removed from the cannular needle 120, and the cutting member 140 is inserted into the cannular needle 120, as depicted in FIG. 8.

Here, the cutting member 140 may be implemented by a single wire. In the present exemplary embodiment, the cutting member 140 may be composed of seven braided wires 144, as mentioned above. The wire-shaped cutting member 140 prepared in this way is flexible enough to tightly surround the flexor retinaculum from below it to above it, or vice versa. Further, since the cutting member 140 has prominences on the surface thereof, it has enough roughness to cut the flexor retinaculum. Furthermore, since the wire-shaped cutting member does not have a conventional blade-like protruding shape for cutting the flexor retinaculum, damage on adjacent cells can be minimized when the cutting member saws the flexor retinaculum in contact with it.

As stated above, if the cannular needle 120 is eliminated after the cutting member 140 is inserted into the cannular needle 12, the cutting member 140 is arranged below the flexor retinaculum 10 in the range from the insertion hole 12 to the exposure hole 14.

Further, as aforementioned above, the cannular needle 120 may be inserted again from the front to the rear of the flexor retinaculum 10 to be positioned above the flexor retinaculum. To be more specific, after the cannular needle 120 is inserted into the skin at the front of the flexor retinaculum 10 and the blunt rod 130 is inserted to above the flexor retinaculum from the front to the rear of the flexor retinaculum 10, the cannular needle 120 is pushed and moved along the blunt rod 130, thus allowing the leading end of the cannular needle 120 to be exposed out of the skin by penetrating the skin.

Thereafter, as depicted in FIG. 10, the cutting member 140 is inserted through the cannular needle 140 from the front to the rear of the cannular needle 120. Then, if the cannular needle 120 is removed from the skin, the cutting member 140 is arranged to surround the flexor retinaculum 10 in a U-shape over the upper and lower portions thereof.

Through these processes, the cutting member 140 can be arranged to surround the flexor retinaculum 10 in a U-shape. Then, by repeatedly giving back-and-forth motion to the cutting member 140 holding both ends thereof, the flexor retinaculum 10 can be cut from the front to the rear of it.

For reference, as stated above, only one through hole is formed at each of the skin in front of the flexor retinaculum 10 and the skin at the rear of it by the cannular needle 120. In the present exemplary embodiment, the cannular needle 120 is inserted into the insertion hole 12 and took out of the exposure hole 14, which are formed in front of and at the rear of the flexor retinaculum 10 by the first used cannular needle 120, respectively, to thereby form the passageway led to the position above the flexor retinaculum 10. Thus, the number of puncture holes formed on the skin can be reduced.

Especially, when both ends of the cutting member 140 are exposed to the rear of the flexor retinaculum 10 as in the present exemplary embodiment, only one exposure hole 14 is formed in the skin at the rear of the flexor retinaculum 10, and by holding both ends of the cutting member 140 and sawing the flexor retinaculum 10, the skin can be prevented from being unnecessarily incised during the process of cutting the flexor retinaculum 10.

For reference, in the present exemplary embodiment, the position below the flexor retinaculum may refer to a position directly below the flexor retinaculum. To be more specific, the position below the flexor retinaculum may refer to a space between the median nerve 11 and the flexor retinaculum 10, as can be seen from the cross section of the wrist shown in FIG. 2. Further, the position above the flexor retinaculum may refer to a position directly over the flexor retinaculum. To be more specific, the position above the flexor retinaculum may refer to a space between a top surface of the flexor retinaculum and the skin.

Moreover, in the process of forming the passageway by inserting the cannular needle from the front to the rear of the flexor retinaculum through the space above or below the flexor retinaculum, the cannular needle needs to be inserted into a space between the flexor retinaculum, the ulnar artery 13 and the median nerve so as not to hurt the ulnar artery 13.

FIG. 13 is a perspective view illustrating a supporting member included in a medical kit for treating carpal tunnel syndrome in accordance with another exemplary embodiment, and FIG. 14 is a diagram for describing the way to use the supporting member.

The medical kit for treating carpal tunnel syndrome in accordance with this another exemplary embodiment is substantially the same as the medical kit in the above-described exemplary embodiment. Like parts will be assigned like reference numerals, and description will be focused on only the distinctive part, i.e., the supporting member added to the medical kit of the prior exemplary embodiment.

Referring to FIG. 13 and FIG. 14, a supporting member 150 is implemented by a hollow pipe which is partially cut out in a lengthwise direction so as to expose the inside thereof upwards.

The supporting member 150 is inserted into the insertion hole 12 and supports the cutting member 140 that passes below the flexor retinaculum 10. Accordingly, in the process of cutting the flexor retinaculum 10 by sawing it with the cutting member 140 while holding both ends thereof, body cells such as the flexor tendon 15 for use in folding fingers or the median nerve 11 located below the flexor retinaculum 10 can be prevented from being injured by the cutting wire 144. Alternatively, the supporting member 140 can be inserted through the exposure hole 14, not the insertion hole 12, and can support the cutting wire 144 from below it.

The supporting member 140 may be equipped with a rotor blade for preventing the supporting member 140 inserted into the insertion hole 12 from being rotated in an axial direction. Occasionally, the rotation of the supporting member can be suppressed simply by means of a tape 20, as in the present exemplary embodiment.

Although exemplary embodiments of the present disclosure are described above with reference to the accompanying drawings, those skilled in the art will understand that the present disclosure may be implemented in various ways without changing the necessary features or the spirit of the present disclosure. Therefore, it should be understood that the exemplary embodiments described above are not limiting, but only an example in all respects. The scope of the present disclosure is expressed by claims below, not the detailed description, and it should be construed that all changes and modifications achieved from the meanings and scope of claims and equivalent concepts are included in the scope of the present disclosure.

INDUSTRIAL APPLICABILITY

The surgical instrument and the medical kit for treating carpal tunnel syndrome in accordance with the exemplary embodiments of the present disclosure can be widely used in conducting an operation for treating the carpal tunnel syndrome.

The invention claimed is:

1. A method for using a medical kit for treating carpal tunnel syndrome by cutting flexor retinaculum, the method comprising the following sequential steps of:
   (i) inserting a hollow cannular needle having a leading end capable of penetrating into skin (a first insertion hole) such that the leading end of the cannular needle is placed at a first position which is either below or above the flexor retinaculum;
   (ii) inserting a blunt rod into the cannular needle placed at the first position;
   (iii) moving the blunt rod from one end of the flexor retinaculum to the other end of the flexor retinaculum so that a tip of the blunt rod protrudes the leading end of the cannular needle;
   (iv) moving the leading end of the cannular needle along the protruded tip of the blunt rod;
   (v) moving further the cannular needle such that the leading end of the cannular needle is exposed from the skin (a first exposure hole);
   (vi) removing the blunt rod out of the cannular needle and placing a first part of a wire-shaped cutting member into the cannular needle placed at the first position such that an end of the first part of the wire-shaped cutting member is extended out of the first exposure hole of the skin;
   (vii) removing the cannular needle leaving the first part of the wire-shaped cutting member placed at the first position;
   (viii) inserting the hollow cannular needle into the skin (a second insertion hole) such that the leading end of the cannular needle is placed a second position, said second position being above the flexor retinaculum when the first position of (i) is below the flexor retinaculum and being below the flexor retinaculum when the first position of (i) is above the flexor retinaculum;
   (ix) inserting the blunt rod into the cannular needle placed at the second position;

(x) moving the blunt rod from the one end of the flexor retinaculum to the other end of the flexor retinaculum so that a tip of the blunt rod protrudes the leading end of the cannular needle;
(xi) moving the leading end of cannular needle along the protruded tip of the blunt rod;
(xii) moving further the cannular needle such that the leading end of the cannular needle is exposed from the skin (a second exposure hole);
(xiii) removing the blunt rod out of the cannular needle and placing a second part of the wire-shaped cutting member into the cannular needle placed at the second position such that an end of the second part of the wire-shaped cutting member is extended out of the second exposure hole of the skin; and
(xiv) removing the cannular needle leaving the second part of the wire-shaped cutting member placed at the second position,
wherein the cutting member is arranged in a passageway formed by the cannular needle both above and below the flexor retinaculum and the cutting member surrounds the flexor retinaculum, and the flexor retinaculum is cut by the cutting member passing through the above and the below of the retinaculum.

2. The method of claim 1, which further comprises, before inserting the hollow cannular needle in step (i) and/or (viii), checking a position of skin through which the cannular needle penetrates into by ultrasonography.

3. The method of claim 1, wherein the first insertion hole and the second insertion hole are a same single hole.

\* \* \* \* \*